(12) United States Patent
Brozik et al.

(10) Patent No.: US 9,157,161 B1
(45) Date of Patent: Oct. 13, 2015

(54) MULTIFUNCTIONAL THIN FILM SURFACE

(75) Inventors: Susan M. Brozik, Albuquerque, NM (US); Jason C. Harper, Rio Rancho, NM (US); Ronen Polsky, Albuquerque, NM (US); David R. Wheeler, Albuquerque, NM (US); Dulce C. Arango, Albuquerque, NM (US); Shawn M. Dirk, Albuquerque, NM (US)

(73) Assignee: Sandia Corporation, Albuquerque, NM (US)

(*) Notice: Subject to any disclaimer, the term of this patent is extended or adjusted under 35 U.S.C. 154(b) by 786 days.

(21) Appl. No.: 13/183,099

(22) Filed: Jul. 14, 2011

Related U.S. Application Data

(63) Continuation-in-part of application No. 12/482,639, filed on Jun. 11, 2009, now abandoned, and a continuation-in-part of application No. 11/762,414, filed on Jun. 13, 2007, now abandoned.

(51) Int. Cl.
C25D 5/10 (2006.01)
C23C 28/00 (2006.01)
C25D 5/48 (2006.01)

(52) U.S. Cl.
CPC .. *C25D 5/48* (2013.01); *C23C 28/00* (2013.01)

(58) Field of Classification Search
CPC ............... C25D 9/02; C25D 5/48; C25D 5/54
USPC ........................... 205/170, 198, 220, 221, 229
See application file for complete search history.

(56) References Cited

U.S. PATENT DOCUMENTS

| | | | |
|---|---|---|---|
| 6,251,595 B1 * | 6/2001 | Gordon et al. | 506/40 |
| 6,652,720 B1 | 11/2003 | Mansouri et al. | |
| 7,550,071 B1 | 6/2009 | Dirk et al. | |
| 2004/0248428 A1 * | 12/2004 | Bureau et al. | 438/780 |

OTHER PUBLICATIONS

Corgier et al., "Diazonium-Protein Adducts for Graphite Electrode Microarrays Modification: Direct and Addressed Electrochemical Immobilization", J. Am. Chem. Soc. (no month, 2005), vol. 127, pp. 18328-18332.*

Liu et al., "Diazonium Salts: Stable Monolayers on Gold Electrodes for Sensing Applications", Journal of Electroanalytical Chemistry (no month, 2007), vol. 600, pp. 335-344.*

Delamar et al., "Covalent Modification of Carbon Surfaces by Grafting of Functionalized Aryl Radicals Produced From Electrochemical Reduction of Diazonium Salts", J. Am. Chem. Soc. (no month, 1992), vol. 114, pp. 5883-5884.*

Corgier et al., "A Versatile Method for Direct and Covalent Immobilization of DNA and Proteins on Biochips", Angew. Chem. Int. Ed. (no month, 2007), vol. 46, pp. 4108-4110.*

(Continued)

*Primary Examiner* — Edna Wong
(74) *Attorney, Agent, or Firm* — Helen S. Baca

(57) ABSTRACT

A thin film with multiple binding functionality can be prepared on an electrode surface via consecutive electroreduction of two or more aryl-onium salts with different functional groups. This versatile and simple method for forming multifunctional surfaces provides an effective means for immobilization of diverse molecules at close proximities. The multifunctional thin film has applications in bioelectronics, molecular electronics, clinical diagnostics, and chemical and biological sensing.

20 Claims, 7 Drawing Sheets

(56) References Cited

OTHER PUBLICATIONS

Kariuki et al., "Formation of Multilayers on Glassy Carbon Electrodes via the Reduction of Diazonium Salts", Langmuir (no month, 2001), vol. 17, pp. 5947-5951.*
Ma et al., "Immobilization of Glycosylated Enzymes on Carbon Electrodes, and Its Application in Biosensors", Microchim Acta (no month, 2005), vol. 150, pp. 21-26.*
Grabar et al., "Preparation and Characterization of Au Colloid Monolayers", Anal. Chem. (no month, 1995), vol. 67, pp. 735-743.*
Dirk, S.M., Potential-directed Assembly of Aryl Iodonium Salts onto Silicon {100} Hydride Terminated and Platinum Surfaces, Langmuir, vol. 21, No. 24, 2005, 10899-10901.
Vase, K. H., Immobilization of Aryl and Alkynyl Groups onto Glassy Carbon Surfaces by Electrochemical Reduction of Iodonium Salts, Langmuir 2005, 21, 8085-8089.
Vase, K. H., Covalent Grafting of Glassy Carbon Electrodes with Diaryliodonium Salts: New Aspects, Langmuir 2007, 23, 3786-3793.
Sakata, T., Anti-Sticking Effect of Organic Dielectric Formed by Electrodeposition in Microelectromechanical-System Structures, Japanese Journal of Applied Physics, vol. 44, No. 7B, 2005. pp. 5732-5735.
Vase, K. H., Electrochemical Surface Derivatization of Glass Carbon by the Reduction of Triaryl- and Alkyldiphensylsulfonium Salts, Langmuir 2008, 24, 182-188.
Kong et al, Direct Electrochemistry of Horseradish Peroxidase Bonded on a Conducting Polymer Modified Glassy Carbon Electrode, Biosensors & Bioelectronics, 19 (2003,) pp. 227-232.
Bourdillon et al, Immobilization of Glucose Oxidase on a Carbon Surface Derivatized by Electrochemical Reduction of Diazonium Salts, J. Electroanal. Chem., 336 (1992), pp. 113-123.
Dequaire, et al., Biotinylation of Screen-Printed Carbon Electrodes through the Electrochemical Reduction of the Diazonium Salt of p-Aminobenzoyl Biocytin, J. Am. Chem. Soc. 1999, 121, pp. 6946-6947.
Harper et al., Electroaddressable Selective Functionalization of Electrode Arrays: Catalytic NADH Detection Using Aryl Diazonium Modified Gold Electrodes, Electroanalysis 19, 2007, No. 12, pp. 1268-1274.
Fan, et al., Protein Pattern Assembly by Active Control of a Triblock Copolymer Monolayer, NANO Letters, 2006, vol. 6, No. 12, pp. 2763-2767.
Liu et al., Diazonium Salts: Stable Monolayers on Gold Electrodes for Sensing Applications, Journal of Electroanalytical Chemistry 600 (2007), pp. 335-344.
Shabani, et al., DNA Immobilization onto Electrochemically Functionalized Si(1 0 0) Surfaces, Talanta, 70 (2006), pp. 615-623.
Polsky, et al., Multifunctional Electrode Arrays: Towards a Universal Detection Platform, Electroanalysis 20, 2008, No. 6, pp. 671-679.
Mamas I. Prodromidis et al, "Enzyme Based Amperometric Biosensers for Food Analysis", Electroanalysis, 2002, vol. 14, No. 4, pp. 241-261.
Benjamin P. Corgier et al, "Diazonium-Protein Adducts for Graphite Electrode Microarrays Modification: Direct and Addressed Electrochemical Immobilization", American Chemical Society, Journal of the American Chemical Society, 2005, vol. 127, pp. 18328-18332.
Serge Cosnier, "Biomolecule immobilization on electrode surfaces by entrapment or attachment to electrochemically polymerized films a review", Biosensors & Bioelectronics, vol. 14 (1999) pp. 443-456.
Yinon Degani et al, "Direct Electrical Communication between Chemically Modified Enzymes and Metal Electrodes, 2. Methods for Bonding Electron-Transfer Relays to Glucose Oxidase and d-Amino-Acid Oxibase", Journal of the American Chemical Society, 1988, vol. 110, pp. 2615-2620.
Michel Delamar et al, "Covalent Modification of Carbon Surfaces by Grafting of Functionalized Aryl Radicals Produced from Electrochemical Reduction of Diazonium Salts", Journal of the American Chemical Society, 1992, vol. 114, pp. 5883-5884.
Alexis Laforgue et al, "Characterization of the Deposition of Organic Molecules at the Surface of Gold by the Electrochemical Reduction of Aryldiazonium Cations," Langmuir, 2005, vol. 21, pp. 6855-6865.
Chang-Soo Lee et al, "Electrically Addressable Biomolecular Functionalization of Carbon Nanotube and Carbon Nanofiber Electrodes", Nano letters, 2004, vol. 4, No. 9, pp. 1713-1716.
Guozhen Liu et al, "An Interface Comprising Molecular Wire and Poly(ethylene glycol) Spacer Units Self-Assembled on Carbon Electrodes for Studies of Protein Electrochemistry", Langmuir, 2006, vol. 22, pp. 7421-7430.
Correspondence—Universal Tools for Biomolecular Attachment to Surfaces, Nature materials, vol. 5, 2006, p. 842.
Ronen Polsky et al, "Diazonium-Functionalized Horseradish Peroxidase immobilized via Addressable Electrodesposition: Direct Electron Transfer and Electrochemical Detection" Langmuir, 2007, vol. 23, pp. 364-366.
Michael P. Stewart et al, "Direct Covalent Grafting of Conjugated Molecules onto Si, GaAs, and Pd Surfaces from Aryldiazonium Salts" Journal of the American Chemical Society, 2004, vol. 126, pp. 370-378.
Alain Adenier et al, "Formation of Polyphenylene Films on Metal Electrodes by Electrochemical Reduction of Benzenediazonium Salts", Chem. Mater. 2006, vol. 18, No. 8, pp. 2021-2029.
Philippe Allongue, et al., "Covalent Modification of Carbon Surfaces by Aryl Radicals Generated from the Electrochemical Reduction of Diazonium Salts", J. Am. Chem. Soc. 1997, vol. 119, No. 1, pp. 201-207.
Franklin Anariba et al, "Mono- and Multilayer Formation by Diazonium Reduction on Carbon Surfaces Monitored with Atomic Force Microscopy "Scratching"", Anal. Chem. 2003, vol. 75, No. 15, pp. 3837-3844.
Marie-Claude Bernard, et al., "Organic Layers Bonded to Industrial, Coinage, and Noble Metals through Electrochemical Reduction of Aryldiazonium Salts", Chem. Mater., 2003, vol. 15, No. 18, pp. 3450-3462.
Paula A. Brooksby et al, "Multilayer Nitroazobenzene Films Covalently Attached to Carbon. An AFM and Electrochemical Study", J. Phys. Chem., B, 2005, vol. 109, No. 18, pp. 8791-8798.
Paula A. Brooksby et al., "Nanoscale Patterning of Flat Carbon Surfaces by Scanning Probe Lithography and Electrochemistry", Langmuir, 2005, vol. 21, No. 5, pp. 1672-1675.
Michel Delamar, et al, "Covalent Modification of Carbon Surfaces by Grafting of Functionalized Aryl Radicals Produced from Electrothemical Reduction of Diazonium Salts", J. Am. Chem. Soc. 1992, vol. 114, pp. 5883-5884.
Alison J. Downard, et al, "Microscale Patterning of Organic Films on Carbon Surfaces Using Electrochemistry and Soft Lithography", Langmuir, 2006, vol. 22, pp. 10739-10746.
Harper, Jason C., et al, "A Multifunctional Thin Film Au Electrode Surface Formed by Consecutive Electrochemical Reduction of Aryl Diazoniurn Salts", Langmuir, 2009, vol. 25, pp. 3282-3288.
Guozhen Liu, et al, "The modification of glassy carbon and gold electrodes with aryl diazonium salt: The impact of the electrode materials on the rate of heterogeneous electron transfer", Chemical Physics. vol. 319, (2005), pp. 136-146.
Guozhen Liu, et al, "An Interface Comprising Molecular Wires and Poly(ethylene glycol) Spacer Units Self-Assembled on Carbon Electrodes for Studies of Protein Electrochemistry", Langmuir, 2006, vol. 22, pp. 7421-7430.
Cyril Louault, et al, "The Electrochemical Grafting of a Mixture of Substituted Phenyl Groups at a Glassy Carbon Electrode Surface", ChemPhysChem, 2008, vol. 9, pp. 1164-1170.
Ali Osman Solak, et al, "Modified Carbon Surfaces as "Organic Electrodes" That Exhibit Conductance Switching", Anal. Chem, 2003, vol. 75, No. 2, pp. 295-305.
Michael P. Stewart. et al. "Direct Covalent Grafting of.Conjugated Molecules onto Si, GaAs. and Pd Surfaces from Aryldiazonium Salts", J. Am. Chem. Soc., 2004, vol. 126. pp. 370-378.

* cited by examiner

MULTIFUNCTIONAL THIN FILM SURFACE

CROSS-REFERENCE TO RELATED APPLICATIONS

This application is a continuation-in-part of application Ser. No. 12/482,639, filed Jun. 11, 2009, now abandoned, and a continuation-in-part of application Ser. No. 11/762,414, filed Jun. 13, 2007, now abandoned, both of which are incorporated herein by reference. This application is related to application Ser. No. 11/930,267, filed Oct. 31, 2007, which is incorporated herein by reference.

STATEMENT OF GOVERNMENT INTEREST

This invention was made with Government support under contract no. DE-AC04-94AL85000 awarded by the U. S. Department of Energy to Sandia Corporation. The Government has certain rights in the invention.

FIELD OF THE INVENTION

The present invention relates to the functionalization of surfaces and, in particular, to a method to prepare a multifunctional thin film on an electrode surface using aryl-onium chemistry.

BACKGROUND OF THE INVENTION

Biosensors make use of the interaction of biological molecules (biomolecules) as a means of sensing an external environment. Biosensors can be very selective, due to the highly specific interactions between biomolecules, for example antibodies and their antigens, cytokines and their cell-surface receptors, enzymes and their substrates, or nucleic acids with themselves or other molecules. The species being sensed in the environment is referred to as the analyte. Therefore, the analyte can be another biological molecule or a chemical that interacts with a biorecognition molecule that has high selectivity for the target analyte. Further, signal transduction methods combined with amplification can provide a biosensor with high sensitivity. These properties—selectivity and sensitivity—make biosensors particularly attractive as analytical devices.

To be useful as a biosensor, the biological interaction must be transduced into a measurable signal. Typically, this interaction can be detected colorimetrically, calorimetrically, or electrochemically. Often, the biological interaction can be converted into an electrochemical signal. In such an electrochemical biosensor, the biorecognition molecule is typically immobilized in a bioselective layer in intimate contact with an electrode which measures the movement of electrons or ions exchanged in the biological interaction. Typically, voltammetry or amperometry can be used to measure the current response to a controlled applied potential that induces an oxidation or reduction process. Alternatively, potentiometry can be used to measure the voltage response to a controlled current.

Functionalization of conducting and semiconducting surfaces is a vital component in the fields of bioelectronics, molecular electronics, clinical diagnostics, and chemical and biological sensing (see I. Willner et al., Biosens. Bioelectron. 22, 1841 (2007); S. J. Oh et al., OMICS 10 327 (2006); R. Byrne and D. Diamond, Nat. Mat. 5, 421 (2006); and J. J. Gooding, Anal. Chim. Acta, 559, 137 (2006)). Of particular interest is the ability to conjugate a surface with two or more different biological, redox active, and/or photo/chemical sensitive molecules. Such multifunctional surfaces would facilitate collection of complicated data sets that would be relevant to cell signaling studies, genomic and proteomic analysis, and the proof-positive identification of biological organisms (see I. Medintz, Nat. Mat. 5, 842 (2006); R. Polsky et al., Electroanalysis 20, 671 (2008); C. A. Rowe-Taitt et al., Biosens. Bioelectron. 15, 579 (2000); C. A. Rowe et al., Anal. Chem. 71, 3846 (1999); and J. C. Harper et al., Langmuir 23, 8285 (2007)). Several methods have been devised and employed to allow surface conjugation including photolithography (see D. Falconnet et al., BioMaterials 27, 3044 (2006); E. Delamarche et al., Adv. Mater. 17, 2911 (2005); and F. L. Yap and Y. Zhang, Biosens. Bioelectron. 22, 775 (2007)), self-assembling monolayers (SAMs) (see E. Katz and I. Willner, Angew. Chem., Int. Ed. 43, 6042 (2004); J. J. Gooding et al., Electroanalysis 15, 81 (2003); and Y. Xiao et al., Science 299, 1877 (2003)), silanes (see W. Senaratne et al., Biomacromolecules 6 2427 (2005); and N. K. Chaki et al., Biosens. Bioelectron. 17, 1 (2002)), stamping (see R. S. Kane et al., Biomaterials 20, 2363 (1999); and Y. Xia and G. M. Whitesides, Angew. Chem., Int. Ed. 37, 550 (1998)), mechanical and/or electrochemical removal of material (see J.-W. Jang et al., Nano Lett. 8, 1451 (2008); G. Liu et al., Acc. Chem. Res. 33, 457 (2000); J. K. Schoer and R. M. Crooks, Langmuir 13, 2323 (1997); and J. K. Schoer et al., J. Phys. Chem. 100, 11086 (1996)), and electropolymerization (see E. Stern et al., Anal. Chem. 78, 6340 (2006); K. Kim et al., J. Chem. Commun., 4723 (2006); and S. Cosnier, Anal. Bioanal. Chem. 377, 507 (2003)). Of these techniques, SAMs based on alkanethiol-gold surfaces have been the most widely used. Several studies utilizing SAMs to form mixed surfaces demonstrating multifunctionality have been published (see S. Choi and W. L. Murphy, Langmuir 24, 6873 (2008); B. M. Lamb et al., Langmuir 24, 8885 (2008); C. Boozer et al., Sens. Actuators, B Chem. 90 22 (2003); R. G. Chapman et al., Langmuir 16, 6927 (2000); C. Roberts et al., J. Am. Chem. Soc. 120, 6548 (1998); and N. Patel et al., Langmuir 13, 6485 (1997)). However, the low enthalpy of the Au—S bond, mobility of the SAMs on gold, tendency of the Au—S bond to oxidize in air and media, and low potential stability window have limited the usefulness of this chemistry (see T. M. Willey et al., Surf. Sci. 576, 188 (2005); and N. T. Flynn et al., Langmuir 19, 10909 (2003).

Electrode surface modification by the electrochemical reduction of aryl diazonium salts is a promising alternative to conventional electrode modification schemes (see M. Delamar et al., J. Am. Chem. Soc. 114, 5883 (1992); P. Allongue et al., J. Am. Chem. Soc. 119, 201 (1997); A. J. Downard, Electroanalysis 12, 1085 (2000); M.-C. Bernard et al., Chem. Mater. 15, 3450 (2003); T.-C. Kuo et al., Electrochem. Solid St. 2, 288 (1999); and F. Anariba et al., Anal. Chem. 75, 3837 (2003)). Electroreduction of the diazonium produces an aryl radical that can then graft to a conducting or semiconducting surface forming a stable covalent bond. This approach has several advantages over alkanethiol-gold chemistry including ease of surface modification, a wider potential window for subsequent electrochemistry, and high stability under long term storage in air and during potential cycling under acidic conditions (see G. Liu et al., J. Electroanal. Chem. 600, 335 (2006); and G. Liu et al., Chem. Phys. 319, 136 (2005)). Diazonium salts with a wide range of substituent groups useful for surface functionalization have been reported including biotin (see M. Dequaire et al., J. Am. Chem. Soc. 121, 6946 (1999)), maleimide (see J. C. Harper et al., Langmuir 24, 2206 (2008)), carboxyl (see B. P. Corgier et al., J. Am. Chem. Soc. 127, 18328 (2005); R. Polsky et al., Biosens. Bioelectron. 23 757 (2008); and R. Polsky et al.,

*Lanmuir* 23, 364 (2007)), amine (see C. S. Lee et al., *Nano Lett.* 4, 1713 (2004); A. Ruffien et al., *Chem. Commun.*, 912 (2003); and A. Shabani et al., *Talanta* 70, 615 (2006)), thiol (see L. T. Nielsen et al., *J. Amer. Chem. Soc.* 129, 1888 (2007)), boronic acid (see R. Polsky et al., *Angew. Chem., Int. Ed.* 47, 2631 (2008)), and azide or alkyne for click chemistry (see D. Evrar et al., *Chem. Eur. J.* (2008), DOI: 10.1002/chem.200801168). Another significant advantage of diazonium electrodeposition chemistry over alkanethiol surfaces is that the surface coverage and density of the resulting film can be controlled by the experimental conditions yielding sub-monolayer to multilayer films (see F. Anariba et al., *Anal. Chem.* 75, 3837 (2003); and P. A. Brooksby and A. J. Downard, *Langmuir* 20, 5038 (2004)). However, it may not always be synthetically straightforward to incorporate the various substituents into a single molecule.

Previously, two-component films prepared from aryl diazonium salts have been formed by simultaneous assembly of two diazonium compounds in a single solution resulting in mixed surfaces (see G. Liu et al., *Chem. Phys.* 319, 136 (2005); G. Liu and J. J. Gooding, *Langmuir* 22, 7421 (2006); and C. Louault et al., *ChemPhysChem* 9, 1164 (2008)) or consecutive deposition leading to stacked structures (see A. Adenier et al., *Chem. Mater.* 18, 2021 (2006); P. A. Brooksby and A. J. Downard, *J. Phys. Chem. B* 109, 8791 (2005); P. A. Brooksby and A. J. Downard, *Langmuir* 21, 1672 (2005); and A. O. Solak et al., *Anal. Chem.* 75 296 (2003)). Poly(dimethylsiloxane) PDMS molds have also been used to pattern assembly of two differing diazoniums via fill-in or consecutive assembly (see A. J. Downard et al., *Langmuir* 22, 10739 (2006)). These works employ electrochemistry, XPS, AFM and other techniques to elucidate the chemical composition of the resulting binary films and the dependence of film properties on the deposition conditions. To date, only one study has utilized diazonium electrodeposition for formation of a multifunctional film towards a specific application. In this work, Liu and Gooding prepared a two-component carbon surface by electroreduction of a mixture containing diazoniums with oligo(phenylethynlene) and poly(ethylene glycol) (PEG) functionality (see G. Liu and J. J. Gooding, *Langmuir* 22, 7421 (2006)). Oligo(phenylethynlene) served as a conductive path to the electrode allowing direct electron transfer to surface immobilized horseradish peroxidase or myoglobin, while PEG served to decrease non-specific adsorption of bovine serum albumin and components of blood serum onto the electrode surface.

However, a need remains for more versatile and simple methods to prepare multifunctional thin films using aryl-onium chemistry.

SUMMARY OF THE INVENTION

The present invention is directed to a method to consecutively or simultaneously deposit different molecules with differing substituent groups to yield stable films that are mixed or stacked in structure and capable of multiple functionalities on a single surface. The method comprises providing a conducting or semiconducting electrode; electrodepositing a first aryl-onium molecule, having a first functional group, onto the surface of the electrode; and grafting a second molecule, having a second functional group, with the electrodeposited first aryl-onium molecule to provide a multifunctional thin film surface. The aryl-onium molecules can comprise aryl diazonium, aryl iodonium, aryl bromonium, or aryl sulfonium. The functional groups can comprise native, modified, or synthetic chem- or bio-recognition molecules, including biotin, maleimide, carboxyl, amine, thiol, boronic acid, azide, or alkyne, that can react with target analytes. The functional groups can comprise an unreactive group that is blocked, protected, or inactive and that can be unblocked, deprotected, or activated prior to reaction with a target analyte. Further, the method can comprise electrochemically grafting two or more additional aryl-onium molecules simultaneously and/or consecutively with the first electrodeposited aryl-onium molecule.

An embodiment of the present invention comprises a multifunctional thin film surface that is capable of immobilizing two diverse molecules on a single gold electrode prepared by consecutive electrodeposition of nitrophenyl and phenylboronic acid pinacol ester diazonium salts. The stacked film enables the dual immobilization of citrate-capped platinum nanoparticles via electrostatic interactions with electro-generated aminophenyl groups and yeast cells via cyclic ester formation between chemically deblocked boronic acid groups and saccharides present in yeast membranes. In addition to electrostatic interactions, the aminophenyl surface can potentially be used with a variety of common homo/heterobifunctional crosslinkers to conjugate other diverse molecules at close proximities to immobilized cells.

This versatile and simple method for forming multifunctional surfaces provides an effective means for immobilization of diverse molecules at close proximities. Such surfaces potentially allow for the immobilization of a variety to diverse molecules including nanoparticles, antibodies, DNA probes, and whole cells on a single surface without the requirement of printing, lithography, or discrete individually addressable electrodes. Possible applications include analysis of cell signaling, cell-cell and host-pathogen interactions, genomic and proteomic analysis, chemical and biological sensing, and chemical research platforms.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 7C shows a SEM image showing PtNPs near the edge of an immobilized yeast cell on a deblocked phenylboronic acid-aminophenyl Au electrode.

DETAILED DESCRIPTION OF THE INVENTION

Figure 1:
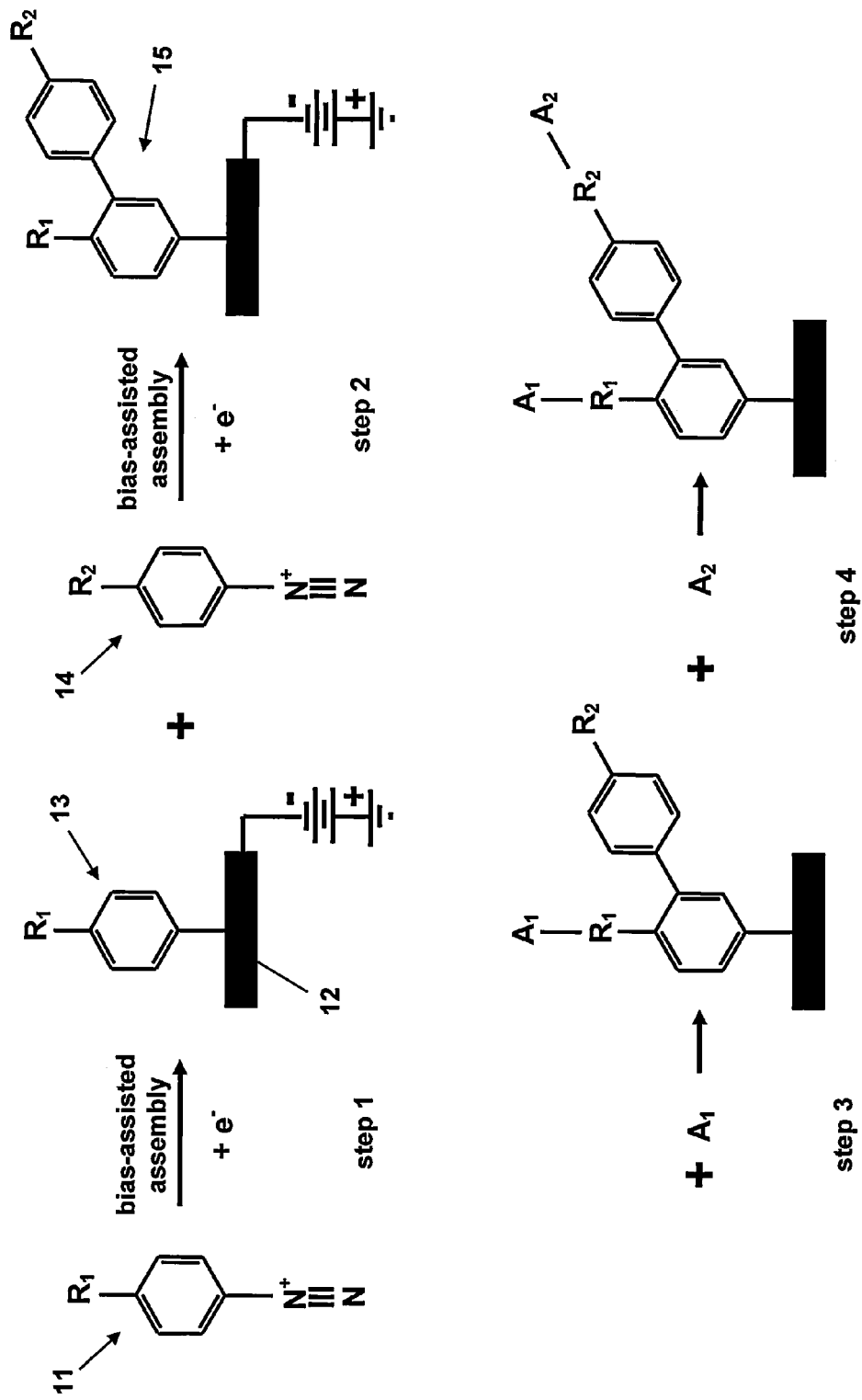
FIG. 1 is a schematic illustration of a method to prepare a multifunctional thin film by the consecutive electrodeposition of separately functionalized aryl-onium salts.

In FIG. 1 is shown a method to prepare a multifunctional thin film on an electrode surface using aryl-onium chemistry according to the present invention. A solution comprising a first aryl-onium salt 11, having a first functional group $R_1$, is provided in a solvent. Any aryl-onium salt, such as aryl diazonium, aryl iodonium, aryl bromonium, or aryl sulfonium, that can graft to a conducting or semiconducting electrode and allows bias-driven reaction and surface functionalization can be used. The first aryl-onium salt 11 is preferably an aryl diazonium salt (as shown), as will be used as an example to describe the invention hereinafter. The first functional group $R_1$ can be a chemical or biological recognition group for immobilization or detection of a first target chemical or biological molecule $A_1$. The functional group $R_1$ can be any native, modified, or synthetic chem- or bio-recognition molecule, such as an antibody, protein, enzyme, DNA, RNA, peptide, whole cell, etc., or chemical group that has selectivity for the target analyte $A_1$. For example, the functional group $R_1$ can be biotin, maleimide, carboxyl, amine, thiol, boronic acid, azide, alkyne, or other chemical group that allows immobilization or binding of a target analyte. Alternatively, $R_1$ can be an unreactive group that is blocked, protected, or inactive but can later be activated towards given chemistries for binding or detecting the target analyte $A_1$. The group $R_1$ can be located on any position on the phenyl ring of the aryl-onium 11.

At step 1, electrochemical reduction of the first aryl-onium salt 11 generates an aryl radical (not shown) with simultaneous loss of nitrogen, as has been described by Stewart et al. (see Stewart et al., *J. Am. Chem. Soc.* 126, 370 (2004)). The aryl radical can then graft to the electrode surface 12 to provide a covalently bound phenyl monolayer 13. The electrode 12 can be a bare conducting or semiconducting electrode or can be coated with a thin film or other surface modification, as long as aryl-onium grafting can occur. For example, the electrode can comprise a metal, such as gold, or a semiconductor, such as silicon or carbon. This assembly can be assisted by applying a negative bias (as shown), or it can be blocked by applying a positive bias. In practice, a plurality of such bound aryl-onium molecules form a chem/bio selective layer on the surface of the electrode. The surface density of the bound aryl-onium molecules can be controlled by the electrodeposition protocol. Advantages to this approach are a highly stable surface, ease of preparation, and the ability to synthesize aryl-onium salts with a wide range of functional groups. Further, the ability to create an aryl-onium-modified surface by the application of a potential bias enables the selective functionalization of closely-spaced, electrically addressable microelectrode surfaces.

A solution containing a second molecule, having a second functional group, is provided in a solvent. The second molecule can comprise any molecule that can graft to the bound first aryl-onium molecule, such as another aryl-onium, alkyl halide, or phosphonium. In general, the second molecule can graft to the bound aryl-onium molecule by electrodeposition, photodeposition, or spontaneous chemical deposition. Preferably, the solution comprises a second aryl-onium salt 14, having a second functional group $R_2$, as shown. Any aryl-onium salt, such as aryl diazonium, aryl iodonium, aryl bromonium, or aryl sulfonium, that can graft to the bound first aryl-onium molecule can be used. The aryl-onium salt is preferably an aryl diazonium salt (as shown). The functional group $R_2$ can be a chemical or biological recognition group for immobilization or detection of an additional target chemical or biological molecule $A_2$. The functional group $R_2$ can be any native, modified, or synthetic chem- or bio-recognition molecule, such as an antibody, protein, enzyme, DNA, RNA, peptide, whole cell, etc., or chemical group that has selectivity for the target analyte $A_2$. For example, the functional group $R_2$ can be biotin, maleimide, carboxyl, amine, thiol, boronic acid, azide, or alkyne. Alternatively, $R_2$ can be an unreactive group that is blocked, protected, or inactive but can later be activated towards given chemistries for binding or detecting the target analyte $A_2$. The group $R_2$ can be located on any position on the phenyl ring of the aryl-onium.

At step 2, consecutive electrochemical grafting of the second aryl-onium molecule to the bound aryl-onium molecule 13 provides a multifunctional thin film surface 15.

At step 3, the first functional group $R_1$ can react with the target analyte $A_1$. Alternatively, the first function group $R_1$ can be an unreactive group that is blocked, protected, or inactive. The unreactive group can be unblocked, converted, deprotected, or activated prior to reaction of the bound aryl-onium electrode with the target analyte.

At step 4, the second functional group $R_2$ can react with the target analyte $A_2$. Alternatively, the second function group $R_2$ can be an unreactive group that is blocked, protected, or inactive. The unreactive group can be unblocked, converted, deprotected, or activated prior to reaction of the bound aryl-onium electrode with the target analyte.

As will be apparent to those skilled in the art, the reactions of the first and second functional groups can be reversed (i.e., the second functional group can first be reacted with the second target analyte, followed by reaction of the first functional group with the first target analyte). Also, two or more molecules in solution can be grafted simultaneously with the first bound aryl-onium molecule at step 2. Alternatively, two or more different molecules can be grafted consecutively from different solutions with the first bound aryl-onium molecule by repeating step 2 for each additional molecule.

Applications of such multifunctional surfaces include immobilization of two or more distinct capture probes allowing detection of two or more analytes. For example, single stranded DNA probes can be immobilized on the same surface with antibodies probes allowing detection of DNA and protein on the same surface. Alternatively, molecules capable of enhancing detection of an analyte can also be incorporated in the multifunctional film. For example, single stranded DNA probes can be immobilized with ruthenium bipyridine. Ruthenium bipyridine can electrocatalytically increase the signal obtained upon oxidation of target DNA bound to the immobilized probe. Further, antibodies, DNA, and/or other probes can be immobilized at close proximities to whole cells immobilized to the multifunction surface. These probes can be used to detect chemicals, signaling molecules, or proteins excreted from the cell(s) in response to a given stimulus in real time.

The use of -onium modified biomolecules for electrochemical biosensing is described in U.S. application Ser. No. 11/762,414, which is incorporated herein by reference. As described therein, an -onium molecule be modified with a biorecognition molecule and immobilized on an electrode can act as a capture molecule for a target analyte of interest. The -onium molecule can be diazonium, iodonium, or sulfonium. The Application describes, as an example, the use of an aryl-diazonium to immobilize horseradish peroxidase that can provide a biorecognition redox-active enzyme. A similar methodology to that used to conjugate a diazonium molecule to a biomolecule can be similarly used with iodonium or sulfonium molecules to synthesize an iodonium- or sulfonium-modified biomolecules (i.e., using carbodiimide, maleimide, etc. coupling chemistries). Further, the mechanism for selectively immobilizing the iodonium- or sulfonium-modified biomolecule onto a conducting or semi-conducting surface by electroreduction is similar for diazonium-modified biomolecules. The common mechanism is the electroreduction of the -onium, leading to generation of a radical species on the biomolecule which can then react with an electron from a conducting or semiconducting surface, resulting in the covalent grafting of the bio-conjugate to the surface. For example, U.S. Pat. No. 7,550,071, to Dirk et al.; and Dirk et al. *Langmuir* 21, 10899 (2005) describe the electrochemical assembly of organic molecules on conducting or semiconducting substrates using iodonium salt precursors. Likewise, Vase et al. describe the electroreduction of diaryl iodoniums with different function groups leading to covalent grafting onto glassy carbon electrodes. See Vase et al., *Langmuir* 21, 8085 (2005); and Vase et al., *Langmuir* 23, 3786 (2007). Similarly, the electroreduction of triaryl sulfoniums with different function groups leads to covalent grafting onto electrodes. See Sakata et al., *Jap. J. Appl. Phys.* 44, 5732 (2005); and Vase et al., *Langmuir* 24, 182 (2008). In general, the biorecognition molecule can be any native, modified, or synthetic biomolecule, such as an antibody, a protein, enzyme, DNA, RNA, peptide, whole cell, etc., that has selectivity for the target analyte. The target analyte can be a chemical or biological analyte, such as a protein, DNA, or small molecule. The electrode can be a bare conducting or semiconducting electrode or can be coated with a thin film or other surface modification, as long as -onium molecule grafting can occur. Appropriate coupling chemistry can be used to conjugate the -onium molecule with the biorecognition molecule to provide an onium-modified biomolecule. Coupling or crosslinking chemistries include, but are not limited to, free amine groups on a protein surface coupled to an -onium molecule that has a carboxyl functional group on the phenyl ring. Alternatively, free carboxyl groups on a protein can conjugate an -onium molecule that has an amine functional group. Other coupling reactions include, for example, coupling free thiols (e.g., cysteine residues) on the biomolecule with a maleimide functional group on diazonium, as well as carbohydrate groups (that might be found on glycosylated protein or a cell surface) that have an affinity for a boronic acid-modified diazonium salt. The immobilized biomolecule can be reacted with a target analyte to provide a captured analyte. The means for detecting the binding reaction of the immobilized biomolecule with the target analyte can be an electrochemical method, such as voltammetry, amperometry, or potentiometry. For example, the electrochemical method can comprise a label-free electrochemical method, such as impedance, or a binding-induced current-potential change.

Figure 2:
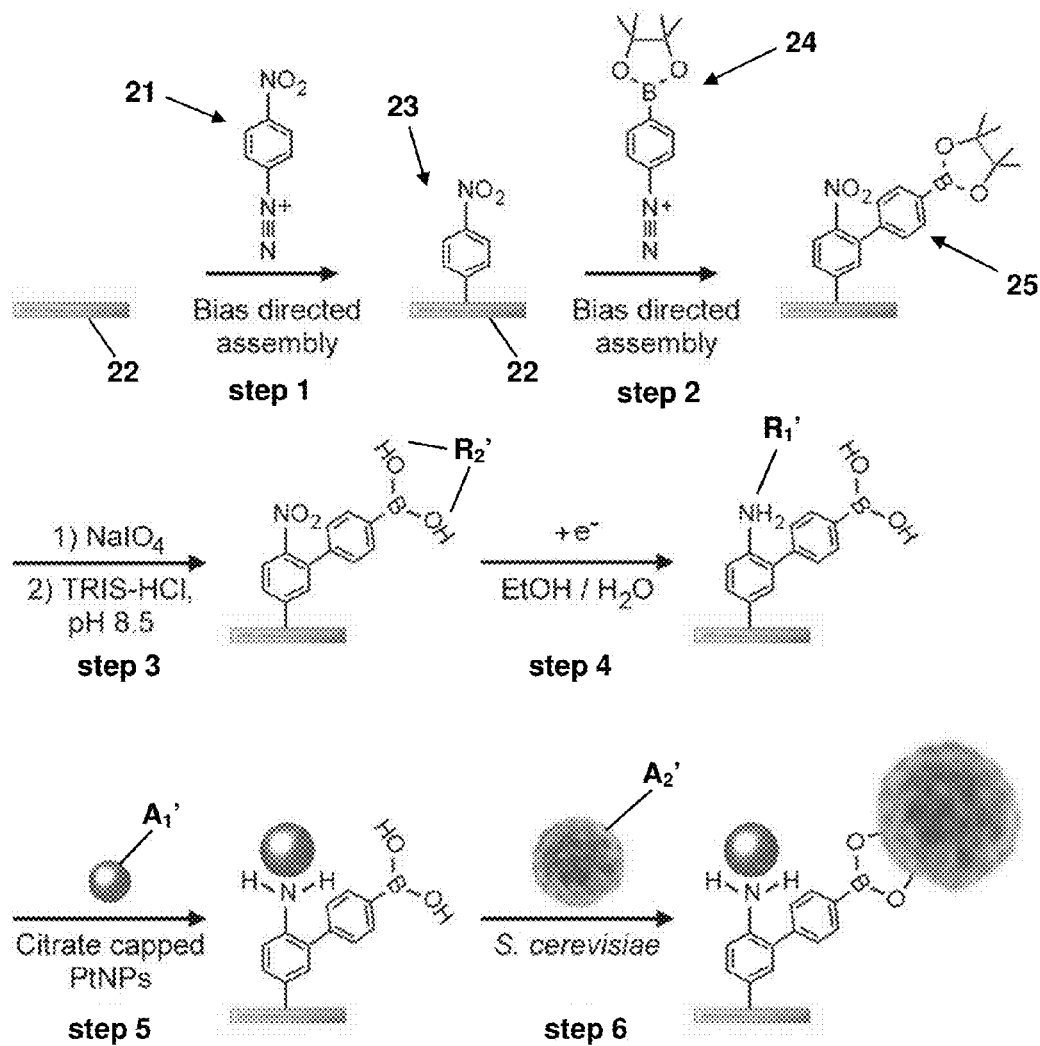
FIG. 2 is a schematic illustration a method to prepare a multifunctional thin film surface capable of immobilizing two diverse molecules on a single gold electrode by consecutive electrodeposition of nitrophenyl and phenylboronic acid pinacol ester diazonium salts.

Multifunctional Thin Film Gold Electrode Surface Formed by Consecutive Electrochemical Reduction of Aryl Diazonium Salts As an example of the present invention, in FIG. 2 is shown a schematic illustration of a method to prepare a stacked multifunctional thin film surface capable of immobilizing two diverse molecules on a single gold electrode by consecutive electrodeposition of nitrophenyl and phenylboronic acid pinacol ester diazonium salts. The method comprises the steps of electrodeposition of nitrophenyl diazonium onto a gold substrate, electrodeposition of pinacol ester phenylboronic acid diazonium forming the stacked thin film, chemical deprotection of phenylboronic acid functional groups, electrochemical reduction of nitrophenyl to aminophenyl functional groups, electrostatic immobilization of citrate capped platinum nanoparticles (PtNPs) to aminophenyl groups, and immobilization of yeast cells via cyclic ester formation between saccharides in the yeast cell membrane and phenylboronic acid groups.

At step 1, a nitrophenyl thin film 23 is assembled onto an electrode 22 via bias-assisted grafting of nitrophenyl diazonium 21. For example, the nitrophenyl thin film can be assembled onto clean gold electrodes using chronoamperometry, linear sweep, or cyclic sweep methods in a solution of 1 mM nitrophenyl diazonium and 0.1 M tetrabutylammonium tetrafluoroborate ($Bu_4NBF_4$) in anhydrous acetonitrile (ACN). After electrodeposition, the electrodes can be briefly rinsed with ACN, followed by an ethanol rinse and a 15 second sonication in ethanol. After sonication, the electrodes can again be rinsed in ethanol and dried under a stream of nitrogen.

At step 2, consecutive electrodeposition of phenyl boronic acid pinacol ester (PBA-PE) diazonium 24 onto the assembled nitrophenyl film 23 forms a multifunctional thin film 25 with both nitro and boronic acid functional groups. For example, phenyl boronic acid pinacol ester diazonium can be prepared as previously reported (see R. Polsky et al., *Angew. Chem., Int. Ed.* 47, 2631 (2008)). The stacked, multifunctional thin film can be formed by consecutive assembly of phenyl boronic acid pinacol ester diazonium onto nitrophenyl modified gold electrodes using cyclic voltammetry in a solution of 1 mM phenyl boronic acid pinacol ester diazonium and 0.1 M $Bu_4NBF_4$ in ACN. Following electrodeposition, the electrodes can again be rinsed, sonicated, and dried as described above.

At step 3, the two functional groups $R_2'$ on the PBA-PE diazonium are then activated towards binding by chemically removing pinacol ester blocking groups. For example, to activate the groups, the nitrophenyl/phenyl boronic acid pinacol ester modified electrodes can be treated with 100 µl of a 50 mM sodium periodate ($NalO_4$) solution (4:1 water:tetrahydrofuran) for 30 min to remove the pinacol blocking ester, and rinsed thoroughly in water. The surface can be conditioned for 1 hour in 100 mM Tris-HCl, pH 8.5, yielding a nitrophenyl/phenyl boronic acid thin film.

At step 4, the nitro groups on the nitrophenyl diazonium are electrochemically reduced to amino groups $R_1'$. For example, conversion of nitrophenyl to aminophenyl groups can be achieved by cyclic voltammetry from −300 to −1300 mV in an ethanol:water (1:9) solution with 0.1 M KCl as electrolyte.

At step 5, the positively charged aminophenyl groups $R_1'$ (e.g., pKa 4.6) electrostatically immobilize negatively charged citrate capped PtNPs $A_1'$ (see E. A. Braude and F. C. Nachod, *Determination of Organic Structures by Physical Methods*; Academic Press: New York, 1955; A. N. Shipway et al., *Langmuir* 16, 8789 (2000); and G. Shustak et al., *Chem. Eur. J.* 13, 6402 (2007)). For example, platinum nanoparticles can be prepared by heating 100 mL of 1 mM dihydrogen hexachloroplatinate ($PtCl_6^{2-}$) in nanopure water to reflux with stirring followed by slow addition of 10 mL of a 38.8 mM aqueous sodium citrate solution. This solution can be stirred under reflux for approximately 1 hour during which the solution will turn from light yellow to black in color. The heat can be removed and the solution allowed to cool to room temperature while stirring. The solution can then be passed through a 100,000 MW cutoff centrifugal filter and washed twice with water. This surface can then be treated with 25 µl of the washed PtNP solution (pH ~5) for 10 minutes followed by rinsing with water and drying with nitrogen to immobilize the PtNPs.

At step 6, the boronic acid groups $R_2'$ are used to immobilize whole cells $A_2'$ through the formation of cyclic esters with saccharides present on yeast cell membranes (see T. D. James et al., *Angew. Chem., Int. Ed.* 35, 1910 (1995); E. Shoji and M. S. Freund, *J. Amer. Chem. Soc.* 124, 12486 (2002); K. D. Pavey et al., *Analyst* 126, 1711 (2001); and N. Soh et al., *Electroanalysis* 15, 1281 (2003)). For example, 50 μl of yeast cells (~1×10$^7$ cells/ml, *S. cerevisiae* strain INVSc1) in 0.1 M sodium phosphate buffer, pH 7.4, can be placed onto the electrodes for five minutes and followed by gentle washing of the electrodes three times with buffer to immobilize the cells.

Electrodeposition of nitrophenyl diazonium films onto gold surfaces has been the subject of several recent studies which show that the electrodeposition protocol can have a profound effect on the order, thickness, and electron transport kinetics of the resulting nitrophenyl film (see J. C. Harper et al., *Electroanalysis* 19, 1268 (2007); H. Uetsuka et al., *Langmuir* 23, 3466 (2007); and J. Haccoun et al., *Prog. Org. Coat.* 63, 18 (2008)). As the nitrophenyl film in this example serves as a conducting layer for the bias assisted assembly of the PBA-PE film, its properties can have a significant effect on the subsequent assembly of the boronic acid film. Therefore, cyclic voltammetry (CV) and ellipsometry were used to characterize the effect of the nitrophenyl film thickness on the subsequent electrodeposition of PBA-PE. All electrochemical measurements were performed on a potentiostat and were measured versus a Ag/AgCl reference (3M NaCl, aqueous solutions) or a Ag/AgNO$_3$ reference (10 mM, non-aqueous solutions, −102 mV vs. ferrocene couple) and a Pt counter electrode. Three different electrodeposition protocols were used to deposit nitrophenyl films onto 5-mm diameter gold disk electrodes: 1) 1 minute chronoamperometric deposition (CA, step to −1 V), 2) linear sweep (LS, 0 to −1 V at 100 mV·s$^{-1}$), and 3) 2 CVs (0 to −1 to 0 V at 100 mV·s$^{-1}$). Following assembly, the nitrophenyl film thickness was measured using ellipsometry. Table 1 shows the average thickness for electrodes prepared from these different methods resulting in submonolayer, monolayer, and 1.5 monolayer nitrophenyl films for the three deposition protocols respectively. In agreement with previous reports, potential sweep methods led to thicker and less ordered films than fixed potential depositions (see J. C. Harper et al., *Electroanalysis* 19, 1268 (2007); and H. Uetsuka et al., *Langmuir* 23, 3466 (2007).

thin film modified gold disk electrodes prepared under various electrodeposition techniques. The second CV cycle for each electrode is omitted for clarity. Submonolayer nitrophenyl modified electrodes (solid black trace in FIG. 3) showed a reductive peak shoulder at −105 mV that is attributed to the electroreduction of the diazonium functional group. This shoulder is not as sharp and is shifted −25 mV compared to that obtained from electrodeposition of PBA-PE diazonium onto a clean Au electrode. The higher overpotential required for reaction and lower relative currents are a manifestation of the higher resistance to electron transfer through the nitrophenyl thin film. Quasi-reversible peaks centered near −550 and −820 mV are also present in CV measurements of the PBA-PE diazonium precursor, 4-aminophenylboronic acid pinacol ester (0.1 M Bu$_4$NBF$_4$ in ACN) and may be redox reactions of pinacol ester hydrolysis products or impurities in the starting material. The irreversible reduction wave at −220 mV is not associated with diazonium grafting. A trend of decreasing PBA-PE diazonium electroreduction currents with increasing nitrophenyl film thickness is observed for the samples prepared from single LS (dotted black trace in FIG. 3) and 2 CV (solid gray trace in FIG. 3) nitrophenyl diazonium depositions. This was expected, as heterogeneous electron transfer through a nitrophenyl film has been shown to decrease as film thickness increases (see J. C. Harper et al., *Electroanalysis* 19, 1268 (2007)). Assembly of PBA-PE onto the nitrophenyl films was verified via ellipsometry measurements following PBA-PE diazonium deposition, as shown in Table 1. Equivalent monolayers were calculated directly from ellipsometry measurements. As expected, the thickest PBA-PE films were deposited onto the thinnest nitrophenyl films due to higher electron transfer kinetics through the nitrophenyl film enhancing PBA-PE diazonium electroreduction and grafting.

The functional groups of the stacked diazonium film were activated towards binding by first removal of the pinacol ester group via chemical deprotection. This was followed by electrochemical reduction of nitro groups to amines. The first reductive sweep in aqueous solution produced a sharp wave corresponding to the six electron reduction of nitrophenyl to aminophenyl. This peak was not observed in subsequent sweeps indicating complete conversion of all electrically accessible nitro groups. The area of the reduction waves corresponds to the total charge transferred during the reaction, and hence, the number of nitro groups electrically accessible to the electrode and the electrolyte solution. Nitro surface

TABLE 1

Effect of diazonium electrodepostion method on stacked surface film thickness

| Nitrophenyl diazonium electrodeposition method | Nitrophenyl film thickness (Å)[a] | Equivalent monolayers (nitrophenyl)[b] | Γ (mol NO$_2$/cm$^2$)[c] | Film thickness after 2 CV B(OH)$_2$ diazonium electrodepostion (Å)[a] | Equivalent monolayers (B(OH)$_2$)[b] |
|---|---|---|---|---|---|
| 1 min CA | 4.0 ± 0.4 | 0.6 ± 0.06 | 0.90 × 10$^{11}$ | 8.0 ± 0.6 | 0.4 ± 0.06 |
| 1 LS | 7.9 ± 1.3 | 1.2 ± 0.20 | 3.0 × 10$^{11}$ | 10.9 ± 1.6 | 0.3 ± 0.16 |
| 2 CV | 10.3 ± 1.8 | 1.5 ± 0.27 | 1.1 × 10$^{10}$ | 12.0 ± 1.0 | 0.2 ± 0.10 |

[a]Standard deviations were calculated from eight or more independent measurements on each of three electrodes sampled per electrodeposition technique
[b]Calculated thickness of a nitrophenyl and a phenylboronic acid pinacol ester monolayer with 70° tilt is approximately 6.7 Å and 10.0 Å, respectively.
[c]Surface concentration calculated from the total charge transferred during the 6 electron nitro to amine reduction.

Figure 3:
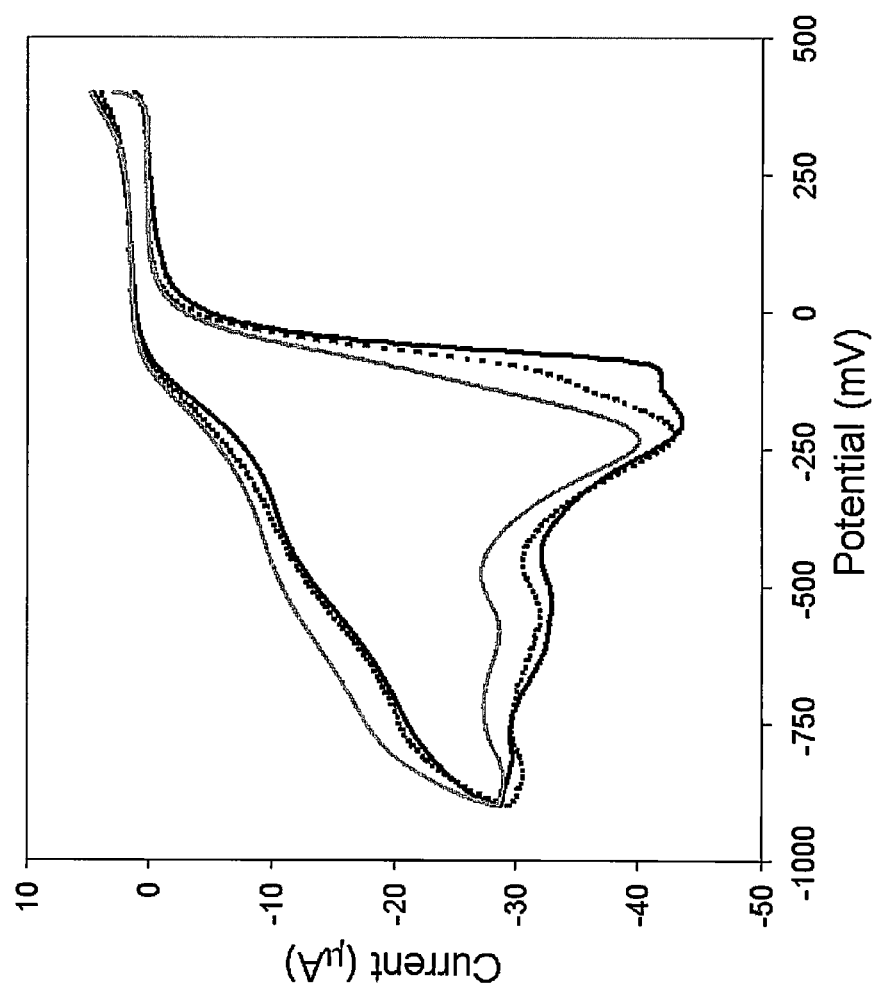
FIG. 3 shows cyclic voltammograms of phenylboronic acid pinacol ester diazonium on nitrophenyl thin film modified gold disk electrodes prepared using various electrodeposition techniques.

The nitrophenyl modified electrodes were subsequently modified with PBA-PE using a 2 CV (0 to −1 to 0 V at 100 mV·s$^{-1}$) electrodeposition from the corresponding diazonium salt. FIG. 3 shows cyclic voltammograms of 1 mM phenylboronic acid pinacol ester diazonium on nitrophenyl concentrations, F, are reported in Table 1. The greatest surface concentration of NO$_2$ corresponds to the nitrophenyl film electrode assembled with 2 CVs and is followed by electrodes prepared from 1 LS, and 1 min CA. This trend agrees with the average nitrophenyl film thickness data obtained from ellipsometry. These surface concentrations are similar to values obtained from nitrophenyl films on Au with similar thicknesses (see J. C. Harper et al., *Electroanalysis* 19, 1268 (2007)).

Figure 4:
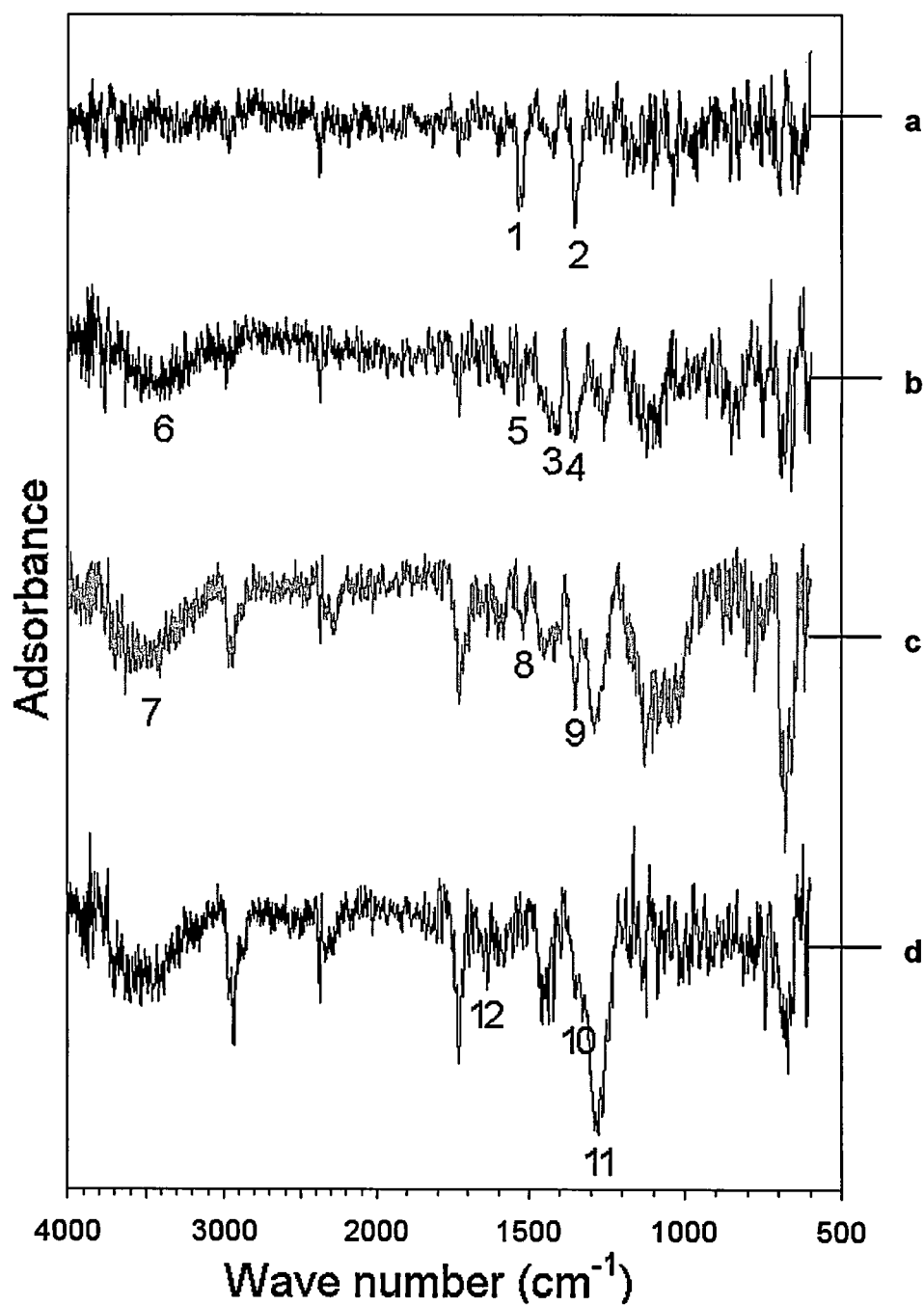
FIG. 4 shows grazing-angle FTIR spectroscopy measurements for gold electrodes prepared according to the method shown in FIG. 2.

Grazing-angle FTIR spectra analysis was further used to study and verify film composition at each stage of preparation. FIG. 4 shows grazing-angle FTIR spectroscopy measurements for gold electrodes prepared according to the method shown in FIG. 2: a) nitrophenyl surface; b) PBA-PE nitrophenyl surface; c) PBA-nitrophenyl surface; d) PBA-aminophenyl surface. All surfaces were prepared from 2 CV electrode positions of the respective diazonium salt(s).

Plot a shows the spectrum measured from a gold surface prepared from a 2 CV nitrophenyl diazonium electrodeposition. Of note are two peaks at 1534 cm$^{-1}$ and 1351 cm$^{-1}$ (labeled peaks 1 and 2) characteristic of the asymmetric and symmetric stretch modes, respectively, of the nitro group. Upon subsequent treatment with a 2 CV PBA-PE diazonium electrodeposition the stacked surface exhibits properties of both boron and nitro functionalities (plot b). The FTIR spectrum shows a clear B-phenyl stretch mode at 1417 cm$^{-1}$ (peak 3) and retains the band at 1351 cm$^{-1}$ (peak 4) which may be the overlap of both the symmetric nitro and B—O stretches. Also present is the asymmetric nitro stretch which has shifted slightly to 1536 cm$^{-1}$ (peak 5). This peak is not present in the FTIR spectra of PBA-PE deposited alone on Au (see R. Polsky et al., *Angew. Chem., Int. Ed.* 47, 2631 (2008)) verifying that the thin film contains both nitro and PBA functional groups. A broad O—H stretch at 3400 cm$^{-1}$ (peak 6) is indicative of some inadvertent hydrolysis. FTIR spectroscopy following chemical deprotection of the pinacol ester group (plot c), showed significant enhancement in the O—H stretch modes at 3400 cm$^{-1}$ (peak 7). Still present are the asymmetric nitro stretch at 1521 cm$^{-1}$ (peak 8) and the symmetric nitro and B—O stretches at 1351 cm$^{-1}$ (peak 9). The FTIR spectrum following electrochemical reduction of nitrophenyl to aminophenyl groups is shown in plot d. The peak at 1351 cm$^{-1}$ (peak 10) is not as pronounced as in previous spectra, indicative of loss of the symmetric nitro stretch while the peak at 1276 cm$^{-1}$ (peak 11), characteristic of the C—N stretch, has increased in intensity. The peak at 1351 cm$^{-1}$ is not completely lost due to remaining B—O stretching. Further evidence of nitro to amine conversion arises from the loss of the asymmetric nitro stretch at 1521 cm$^{-1}$ (peak 8) and the appearance of a peak at 1634 cm$^{-1}$ (peak 12) characteristic of the NH$_2$ deformation band.

Figure 5:
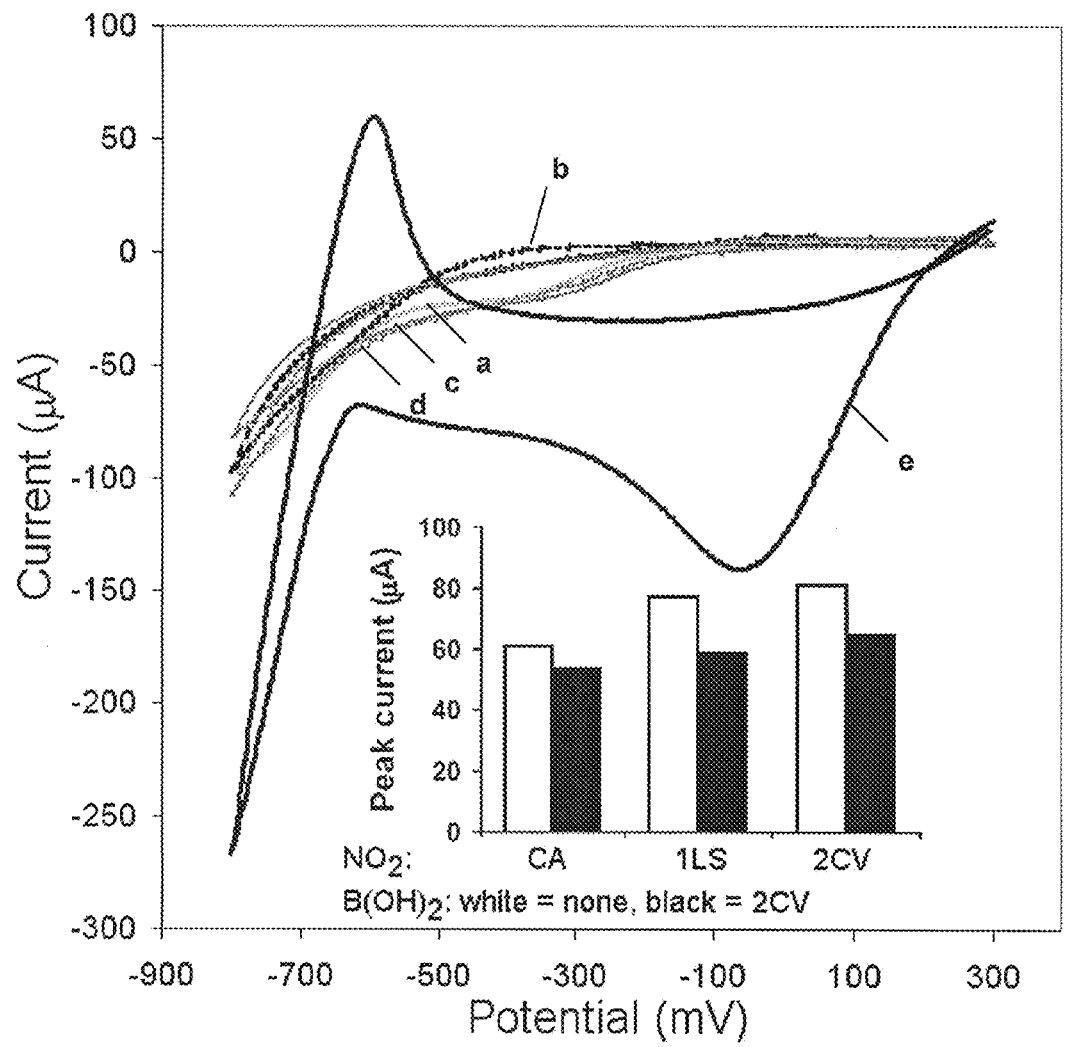
FIG. 5 shows cyclic voltammograms of 1 mM $H_2O_2$ in 50 mM NaPB for films formed via 2CV electrodeposition of nitrophenyl diazonium.

Use of PtNPs served as a means to determine the accessibility of the aminophenyl groups following PBA-PE deposition, to measure the conductive properties of the stacked thin film, and allowed for visualization of PtNP binding in relation to immobilized yeast cells via microscopy. The affinity of the aminophenyl film towards electrostatic immobilization of PtNPs was initially investigated without subsequent assembly of the PBA-PE film. FIG. 5 shows cyclic voltammograms of 1 mM H$_2$O$_2$ in 50 mM NaPB at pH 7.4 and a sweep of v=100 mV·s$^{-1}$: a) clean Au electrode; b) nitrophenyl Au; c) aminophenyl Au; d) PtNP treated nitrophenyl Au; and e) PtNP treated aminophenyl Au. All films were formed via 2CV electrodeposition of nitrophenyl diazonium. The inset shows catalytic H$_2$O$_2$ reduction peak currents from PtNP treated Au surfaces with varying nitrophenyl diazonium electrodeposition procedure (white bars), and phenylboronic acid-aminophenyl stacked Au surfaces with varying nitrophenyl diazonium and constant 2CV phenylboronic acid pinacol ester electrodeposition (black bars).

Figure 6:
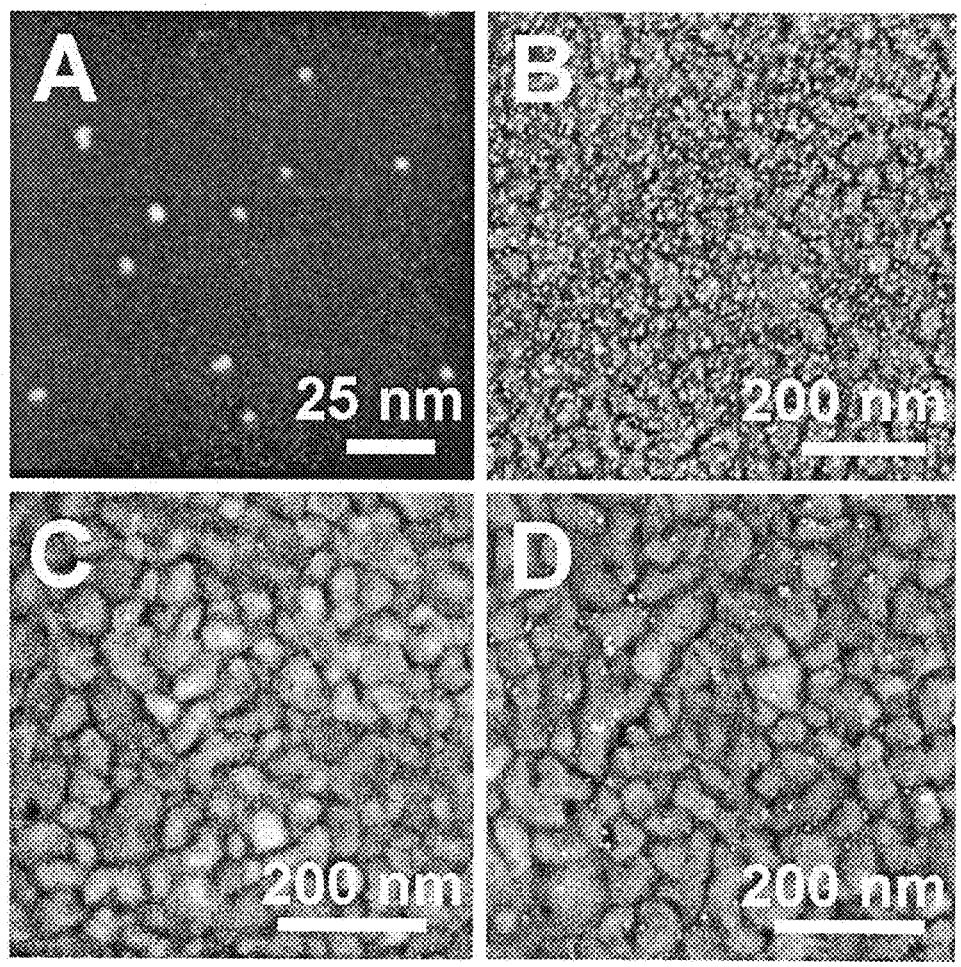
FIG. 6 shows: A) TEM image of citrate capped catalytic PtNPs; B) SEM images of PtNP treated aminophenyl Au surface; C) PtNP treated phenylboronic acid-nitrophenyl stacked surface; and D) PtNP treated phenylboronic acid-aminophenyl stacked surface.

The clean gold electrode (plot a), nitrophenyl film modified electrode (plot b, 2CV electrodeposition), and aminophenyl film modified electrode (plot c, 2CV electrodeposition) showed no significant electrocatalytic peroxide reduction currents and only moderate background currents attributed to reduction of dissolved oxygen in the electrolyte solution. Similarly, the nitrophenyl film prepared from a 2 CV electrodeposition followed by a 10 minute treatment with PtNPs (plot d) showed no electrocatalytic currents. In contrast, the aminophenyl surface treated with PtNPs followed by thorough rinsing (plot e, 2CV electrodeposition) yielded a cathodic current wave near −70 mV characteristic of PtNP catalyzed H$_2$O$_2$ reduction (see K.-F. Chow et al., *Amer. Chem. Soc.* 130, 7544 (2008); and R. Polsky et al., *Anal. Chem.* 78, 2268 (2006)). This NP catalyzed H$_2$O$_2$ reduction is highly dependent on the NP size with optimal currents obtained from 2-4 nm diameter particles (see O. Antoine et al., *J. Electroanal. Chem.* 499, 85 (2001); K. Kinoshita, *J. Electrochem. Soc.* 137, 845 (1990); and R. Polsky et al., *Chem. Commun.*, 2741 (2007)). TEM imaging was used to determine the size distribution of the synthesized PtNP, as shown in FIG. 6A. As expected from the efficient peroxide reduction currents, the PtNPs were 2.7±0.4 nm in diameter. The PtNP modified aminophenyl surface was also stable to successive rinses, drying, and treatment with 300 mM sodium citrate solution. Additionally, these currents demonstrate that the deposited thin film remains conductive allowing for subsequent electrochemical measurements.

Both the number of aminophenyl groups and de-blocked phenylboronic acid (PBA) groups were shown to affect PtNP immobilization. The inset of FIG. 5 shows the electrocatalytic peak currents obtained from H$_2$O$_2$ reduction at aminophenyl Au surfaces prepared from 1 min CA, 1 LS, and 2 CV nitrophenyl depositions (white bars). A strong correlation is observed between the ellipsometry data, NO$_2$ surface concentrations, and electrocatalytic peak currents showing that increasing film thickness and density lead to higher PtNP loading. The most significant increase in current was obtained between the surfaces prepared from 1 min CA and 1 LS deposition. This indicates that increasing the aminophenyl surface coverage from submonolayer to monolayer had a greater impact on PtNP loading than increasing the aminophenyl group surface density (1 LS and 2 CV samples). Formation of PBA films onto aminophenyl films negatively impacted the affinity of the underlying aminophenyl film towards PtNP immobilization (see inset to FIG. 5, black bars). All stacked PBA-aminophenyl films showed lower catalytic peak currents than aminophenyl films prepared under identical nitrophenyl electrodeposition protocols. This is likely due to blocking of portions of the aminophenyl film onto which the PBA was assembled. The decrease in catalytic currents between PBA-aminophenyl and aminophenyl films prepared from a 1 min CA nitrophenyl deposition was half that obtained between PBA-aminophenyl and aminophenyl films prepared from 1 LS or 2 CVs nitrophenyl depositions. As aminophenyl films prepared from 1 min CA electrodepositions are submonolayer, a substantial portion of PBA presumably assembled onto the free Au surface providing a less detrimental impact on PtNP immobilization. Despite the relatively lower PtNP loading and catalytic currents on PBA-aminophenyl surfaces, submonolayer PBA films permitted access to a substantial portion of the underlying aminophenyl layer providing significant catalytic peak currents that increase for electrodes with higher aminophenyl film thickness and lower PBA thickness.

PBA-PE films thicker than submonolayer could be obtained by changing the conditions of electrodeposition. For example, a 2 CV nitrophenyl diazonium electrodeposition followed by a 5 CV PBA-PE diazonium electrodeposition yielded film thicknesses of 9.3±2.5 Å and 26.0±0.9 Å, respectively, formed a 1.7 equivalent monolayer PBA-PE thin film. Following removal of the pinacol ester blocking group and electrochemical reduction of nitro to amino groups, the surface was treated with PtNP solution. CVs in peroxide solution revealed that these stacked surfaces were not effective at capturing PtNPs. This could be due to the approximately 30% lower ($8.0\pm2.0\times10^{11}$ mol $NO_2 \cdot cm^{-2}$) nitro to amine conversion compared to surfaces prepared from a 2 CV nitrophenyl and 2 CV PBA-PE diazonium electrodeposition. It is also likely that the thicker PBA films have sterically hindered PtNP access to the underlying reduced nitrophenyl film.

De-blocked PBA surfaces (pKa ~8) do show minor non-specific binding of citrate capped PtNPs, generating a peroxide catalytic reduction peak that is 23% of that obtained from a similarly treated aminophenyl surface (see J. Yan et al., *Tetrahedron* 60, 11205 (2004)). These results are also depicted in the SEM images shown in FIG. 6. PtNPs are found at high density on the aminophenyl film (FIG. 6B, 2 CV nitrophenyl diazonium electrodeposition) while the de-blocked PBA-nitrophenyl film shows very few immobilized PtNPs (FIG. 6C, 2 CV nitrophenyl, 2 CV PBA-PE diazonium electrodeposition). The PtNP treated PBA-aminophenyl stacked surface shows a large number of immobilized particles (FIG. 6D, 2 CV nitrophenyl, 2CV PBA-PE diazonium electrodeposition), however the density is not as high as that obtained from the aminophenyl surface alone. As access to the underlying aminophenyl surface was demonstrated by electrostatic interactions with citrate capped PtNPs, common amine conjugation methods including carbodiimide chemistry or homo/hetero-bifunctional crosslinkers can be used to immobilize other diverse molecules to the aminophenyl surface.

The order in which the functional groups are activated is important as $IO_4^-$, used to remove the pinacol ester, can also oxidize amine groups forming hydroxylamine or nitro groups. Treatment of an aminophenyl surface with the $IO_4^-$ pinacol ester deprotection solution for 30 minutes converted 22% of amino groups back to nitro groups (assuming complete oxidation) as determined by integration of the nitro reduction peak before and after $IO_4^-$ treatment. The percentage of reacted amine groups may be higher if incomplete oxidation occurred forming hydroxylamine groups. These reacted amines are likely those most accessible to the $IO_4^-$ solution on the surface of the thin film. Following $IO_4^-$ treatment the partially oxidized aminophenyl surface was ineffective at capturing PtNPs as determined by CV in $H_2O_2$ solution. Presumably loss of these surface amino groups was sufficient to prevent electrostatic binding of the citrate capped PtNPs to the Au electrode surface.

Figure 7:
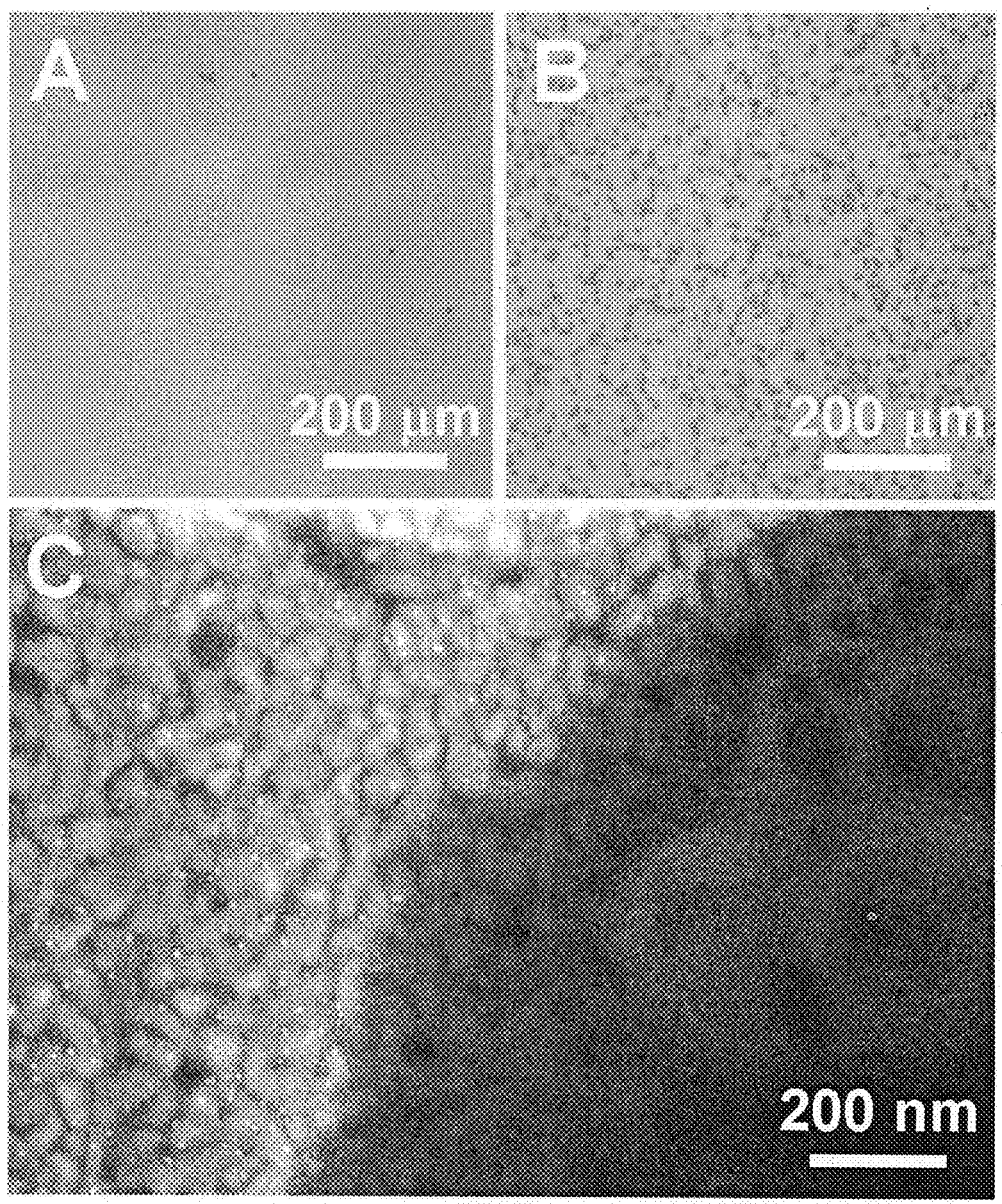
FIG. 7 shows white light images of: A) pinacol ester blocked phenylboronic acid-aminophenyl; and B) de-blocked phenylboronic acid-aminophenyl Au electrodes treated with yeast in nanopure water and rinsed with 0.1 M TRIS-HCl, pH 8.5.

The affinity for yeast cell adhesion to the stacked thin film was determined for the blocked PBA-PE-aminophenyl film and the de-blocked PBA-aminophenyl film after a brief treatment with yeast cells in buffer. As presented in the microscope images in FIG. 7, the blocked PBA-PE surface (FIG. 7A) had very few cells non-specifically bound to the surface while many yeast cells adhered to the de-blocked PBA-aminophenyl surface (FIG. 7B). This is consistent with previous studies showing capture of sugars and cells at boronic acid modified surfaces and shows that the underlying aminophenyl layer has no significant effect on yeast cell adhesion (see R. Polsky et al., *Angew. Chem., Int. Ed.* 47, 2631 (2008); T. D. James et al., *Angew. Chem., Int. Ed.* 35 1910 (1995); E. Shoji and M. S. Freund, *J. Amer. Chem. Soc.* 124, 12486 (2002); K. D. Pavey et al., *Analyst* 126, 1711 (2001); and N. Soh et al., *Electroanalysis* 15, 1281 (2003)). FIG. 7C demonstrates the utility of the multifunctional thin film for immobilization of both PtNPs and the capture of yeast cells. This SEM image shows PtNPs in close proximity to an immobilized yeast cell, seen as a dark shadow, on a de-blocked PBA-aminophenyl functionalized Au electrode. All electrodes were prepared from a 2 CV nitrophenyl electrodeposition followed by a 2 CV PBA-PE diazonium electrodeposition. Although not visible through the yeast cell, PtNPs are expected to exist beneath the cell at a density similar to that observed surrounding the cell. The close proximity of captured PtNPs and yeast cells on this surface demonstrate ideal immobilization conditions for placement of cell monitoring probes that may detect chemicals, signaling molecules, or proteins excreted from the cell(s).

The present invention has been described as a method to prepare a multifunctional thin film surface. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method to prepare a multifunctional thin film surface, comprising:
   i) providing a conducting or semiconducting electrode,
   ii) electrodepositing a first aryl-onium molecule, having a first functional group, onto a surface of the electrode, wherein the first functional group is selective to a first target analyte, thereby providing an immobilized film of the first aryl-onium molecule,
   iii) electrochemical grafting a second molecule, having a second functional group, to the electrodeposited first aryl-onium molecule, wherein the second functional group is selective to a second target analyte and the second functional group is different than the first functional group, and wherein the electrochemical grafting provides a submonolayer of the second molecule grafted on the immobilized film,
   iv) treating a surface of the submonolayer with one or more whole cells, wherein the second target analyte is present on at least one of the one or more whole cells,
   v) reacting the second functional group with the second target analyte present on the at least one of the one or more whole cells, thereby providing the at least one of the one or more whole cells immobilized on the submonolayer of the second molecule, and
   vi) reacting the first functional group with the first target analyte,
   thereby providing the multifunctional thin film surface conjugated to the at least one of the one or more whole cells and the first target analyte.

2. The method of claim 1, wherein the second molecule comprises an aryl-onium molecule.

3. The method of claim 1, wherein the first aryl-onium molecule comprises an aryl diazonium molecule.

4. The method of claim 3, wherein the aryl diazonium molecule comprises nitrophenyl diazonium or boronic acid pinacol ester diazonium.

5. The method of claim 1, wherein the first aryl-onium molecule comprises an aryl iodonium, aryl bromonium, or aryl sulfonium molecule.

6. The method of claim 1, wherein at least one of the first and second functional groups comprises a native, modified, or synthetic chem- or bio-recognition molecule.

7. The method of claim 1, wherein at least one of the first and second functional groups comprises an antibody, a protein, an enzyme, a DNA, a RNA, a peptide, a whole cell, or a chemical group that has selectivity for the first target analyte or for the second target analyte.

8. The method of claim 1, wherein at least one of the first and second functional groups comprises biotin, maleimide, carboxyl, amine, thiol, boronic acid, azide, alkyne, or other chemical group that allows binding or immobilization of the first target analyte or of the second target analyte.

9. The method of claim 1, wherein the first functional group comprises an unreactive group that is blocked, protected, or inactive.

10. The method of claim 9, wherein the method further comprises unblocking, deprotecting, or activating the first functional group prior to reacting the first functional group with the first target analyte.

11. The method of claim 1, wherein the second functional group comprises an unreactive group that is blocked, protected, or inactive.

12. The method of claim 11, wherein the method further comprises unblocking, deprotecting, or activating the second functional group prior to reacting the second functional group with the second target analyte.

13. The method of claim 1, wherein the surface of the electrode comprises metal, carbon, or silicon.

14. The method of claim 1, further comprising at least one additional aryl-onium molecule that is simultaneously or consecutively electrodeposited with the first aryl-onium molecule.

15. The method of claim 1, further comprising at least one additional molecule that is grafted to the first aryl-onium molecule simultaneously or consecutively with the second molecule.

16. The method of claim 1, wherein the multifunctional thin film surface comprises

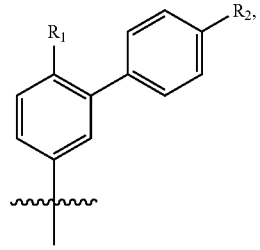

wherein $R_1$ is the first functional group and $R_2$ is the second functional group, and each of $R_1$ and $R_2$ can be located on any position on its respective phenyl ring.

17. The method of claim 16, wherein $R_1$ comprises a nitro or amino functionality and $R_2$ comprises a boron functionality.

18. The method of claim 1, wherein the submonolayer has an average thickness that is less than about 10 Å.

19. The method of claim 18, wherein steps ii) and iii) provides the multifunctional thin film surface comprising the immobilized film of the first aryl-onium molecule having an average thickness that is about 10 Å and the submonolayer of the second molecule having an average thickness that is about 2 Å.

20. The method of claim 18, wherein the submonolayer has an average thickness that is of from about 1.7 Å or greater and is less than about 4.0 Å.

* * * * *